United States Patent [19]
Hujimaki

[11] Patent Number: 5,702,423
[45] Date of Patent: Dec. 30, 1997

[54] TESTING DEVICE IN A LOW-VOLTAGE, LOW-FREQUENCY BEAUTIFYING APPARATUS FOR DETECTING LEAD CORD DISCONTINUITIES

[75] Inventor: Kumiko Hujimaki, Kitakatsushika-gun, Japan

[73] Assignee: Mesotes Co. Ltd., Chiba, Japan

[21] Appl. No.: 652,539
[22] PCT Filed: Sep. 20, 1995
[86] PCT No.: PCT/JP95/01869
  § 371 Date: Jun. 3, 1996
  § 102(e) Date: Jun. 3, 1996
[87] PCT Pub. No.: WO96/10438
  PCT Pub. Date: Apr. 11, 1996

[30] Foreign Application Priority Data

Oct. 3, 1994 [JP] Japan ................ 6-013298 U

[51] Int. Cl.$^6$ ................................ A61N 1/00
[52] U.S. Cl. ................................ 607/2
[58] Field of Search ................ 604/28; 607/2, 607/72, 109, 140, 153; 128/639–641, 696, 734–735, 741

[56] References Cited

U.S. PATENT DOCUMENTS

| | | | |
|---|---|---|---|
| 2,301,567 | 11/1942 | Morse | 604/20 |
| 2,837,041 | 3/1958 | Pierson | 128/734 |
| 3,976,055 | 8/1976 | Monter et al. | 128/641 |
| 4,160,447 | 7/1979 | Teshima et al. | 128/735 |
| 5,273,033 | 12/1993 | Hoffman | 607/72 |

FOREIGN PATENT DOCUMENTS

| | | |
|---|---|---|
| 54-147680 | 11/1979 | Japan. |
| 1144053 | 10/1989 | Japan. |
| 5293186 | 11/1993 | Japan. |

Primary Examiner—William E. Kamm

[57] ABSTRACT

A disconnection checker for lead cords used in low-voltage output type low-frequency beautifying devices. In the upper face of a main body of the beautifying device is a terminal for checking whether each lead cord is disconnected or not when a jack of the lead cord is inserted therein. In the vicinity of the terminal for checking disconnection, an LED lamp lights when the lead cord is not disconnected. Thus, by using the disconnection checker, use of disconnected lead cords is prevented.

16 Claims, 4 Drawing Sheets

TESTING DEVICE IN A LOW-VOLTAGE, LOW-FREQUENCY BEAUTIFYING APPARATUS FOR DETECTING LEAD CORD DISCONTINUITIES

TECHNICAL FIELD

This application is a 371 of PCT/JP95/01869 filed Sep. 20, 1995.

This invention relates to a disconnection checker for checking disconnection of lead cords in low-voltage output type low-frequency beautifying apparatuses whose output is about 1 mA, 6–9V.

BACKGROUND ART

Since the output voltages of low-frequency beautifying apparatuses generally used are high, the voltage can be felt by the body by contacting the lead to skin. If the skin feels the voltage, it is readily known that the lead cord is not disconnected. When the output voltage is abnormal, the circuit is automatically opened by fusion of a fuse or the like, thereby safety is assured.

However, with the conventional low-voltage output type low-frequency beautifying apparatuses whose output is about 1 mA, 6–9V, since the output voltage from the beautifying apparatus is low, it cannot be known from the feeling of the body whether a low-frequency current is conducted through the human body. Further, the beautifying apparatuses are not provided with a checker for checking disconnection of lead cords.

Thus, the conventional low-voltage output type low-frequency beautifying apparatuses whose output is about 1 mA, 6–9V have a drawback in that it is impossible to confirm disconnection of lead cords.

An object of the present invention is to overcome the above-mentioned problem in the prior art and to provide a disconnection checker for checking disconnection of lead cords in low-voltage output type low-frequency beautifying apparatuses, by which disconnection of lead cords can easily be checked.

SUMMARY OF THE INVENTION

In a first aspect of the present invention, the above-mentioned object is attained by providing a disconnection checker in low-voltage output type low-frequency beautifying apparatuses which carry out beautification by attaching two leads to a human body, which leads are connected to a lead cord, and passing low-voltage and low-frequency current through the leads, said disconnection checker comprising a terminal for checking disconnection arranged in a main body of said low-voltage output type low-frequency beautifying apparatus, and indicator means connected to said terminal for checking disconnection, wherein whether the lead cord is disconnected or not is known from an indication of said indicator means when a jack of said lead cord is inserted into said terminal for checking disconnection and said two leads connected to said lead cord are short-circuited.

With this constitution according to the first aspect of the present invention, when the jack is inserted into the terminal for checking disconnection and the two leads are contacted each other, which leads are connected to a lead cord, a circuit driving the indicator means connected to the terminal for checking disconnection is closed such that the indicator means is operated, or the above-mentioned circuit is not closed so that the indicator means remains non-operated.

According to the above-mentioned first aspect of the present invention, whether the lead cord is disconnected or not can be easily, quickly and surely checked by merely inserting a jack of the lead cord into a terminal for checking disconnection provided in a main body of the low-voltage output type low-frequency beautifying apparatus, short-circuiting the two leads and confirming the indication from the indicator means. Therefore, the lead cords which are not disconnected can be used as they are, and it is ordered that the lead cords which are disconnected be replaced. Thus, by using the disconnection checker, erroneous use of a disconnected lead cord is prevented, so that the use of lead cords which are not disconnected is assured for passing low-frequency electric current through a human body, even with a low-voltage type low-frequency beautifying apparatus.

The second aspect of the present invention provides a disconnection checker in low-voltage output type low-frequency beautifying apparatuses which carry out beautification by attaching two leads to human body, which leads are connected to a lead cord, and passing low-voltage and low-frequency current through the leads, said disconnection checker comprising a circuit for checking disconnection having a power source and indicator means, which circuit for checking disconnection is formed in a low-frequency current-supplying circuit of said low-voltage output type low-frequency beautifying apparatus through a change-over switch, wherein whether the lead cord is disconnected or not is known from indication of said indicator means when said change-over switch is switched to said circuit for checking disconnection and said two leads connected to said lead cord are short-circuited.

With this constitution according to the second aspect of the present invention, when the change-over switch is switched to the circuit for checking disconnection and the two leads are contacted each other, which leads are connected to a lead cord, the circuit for checking disconnection driving the indicator means is closed such that the indicator means is operated, or the above-mentioned circuit is not closed so that the indicator means remains non-operated.

According to the second aspect of the present invention, whether the lead cord is disconnected or not can be easily, quickly and surely checked by merely switching the change-over switch to the disconnection checking circuit, short-circuiting the two leads and confirming the indication from the indicator means. Especially, with the constitution according to the second aspect of the present invention, unlike the first aspect of the present invention, whether the respective lead cord is disconnected or not can be checked without inserting a jack of the lead cord into a terminal for checking disconnection, which is very convenient. Thus, by using the disconnection checker, to erroneously use a disconnected lead cord is prevented, so that it is assured to use lead cords which are not disconnected for passing low-frequency electric current through human body, even with a low-voltage type low-frequency beautifying apparatus.

In the first and second aspects of the present invention, light-emitting devices such as LED lamps, sound-making devices such as buzzers, electric current-measuring devices such as ampere meters may be employed as the indicator means. In cases where an LED lamp is employed, the LED lamp is lighted when the lead cord is not disconnected, and is not lighted if the lead cord is disconnected. In cases where a buzzer is employed, the buzzer sounds when the lead cord is not disconnected, and does not sound if the lead cord is disconnected. In cases where an ampere meter is employed, the hand of the ampere meter moves when the lead cord is not disconnected, and does not move if the lead cord is disconnected. By such indicator means, whether the lead cord is disconnected or not can be easily known with eyes or ears. These indicator means may be employed in combination.

Thus, by using the disconnection checker according to the present invention, whether the lead cord is disconnected or not can be checked before performing the beautifying operation, so that to erroneously use a disconnected lead cord is prevented. Therefore, it is assured that low-frequency current is passed through human body to perform low-frequency beautifying operation, even with a low-voltage output type low-frequency beautifying apparatus.

BEST MODE FOR CARRYING OUT THE INVENTION

The present invention will now be described in more detail referring to the appended drawings.

Figure 1:
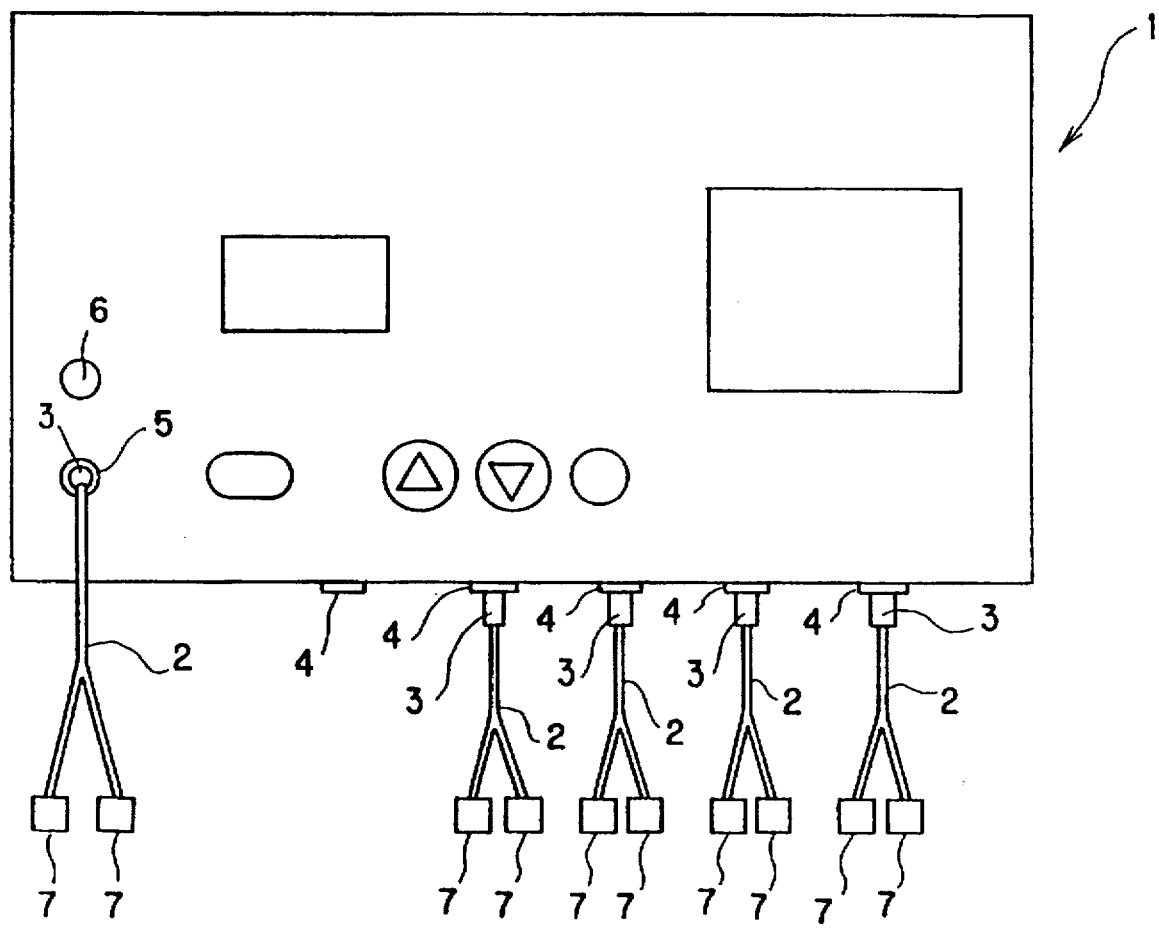
FIG. 1 is a plan view showing the entirety of an embodiment of the disconnection checker of lead cords in low-voltage output type low-frequency beautifying apparatuses, according to the present invention.

FIG. 1 is a plan view showing a preferred position of arranging a disconnection checker of lead cords in a box type low-voltage output type low-frequency beautifying apparatus. In the front face of a main body 1 of the low-voltage output type low-frequency beautifying apparatus, a plurality of terminals 4 into which a jack 3 of each of a plurality of lead cords 2 corresponding to a prescribed sites of human body to be beautified are formed.

On the other hand, in the upper face of the main body 1 of the low-voltage output type low-frequency beautifying apparatus, a terminal 5 for checking disconnection of the lead cords 2 is provided, into which the jack 3 of the lead cords 2 is inserted. Further, in the vicinity of the terminal 5 for checking disconnection, an indicator 6, which is triggered when the lead cords are not disconnected, is provided.

Figure 2:
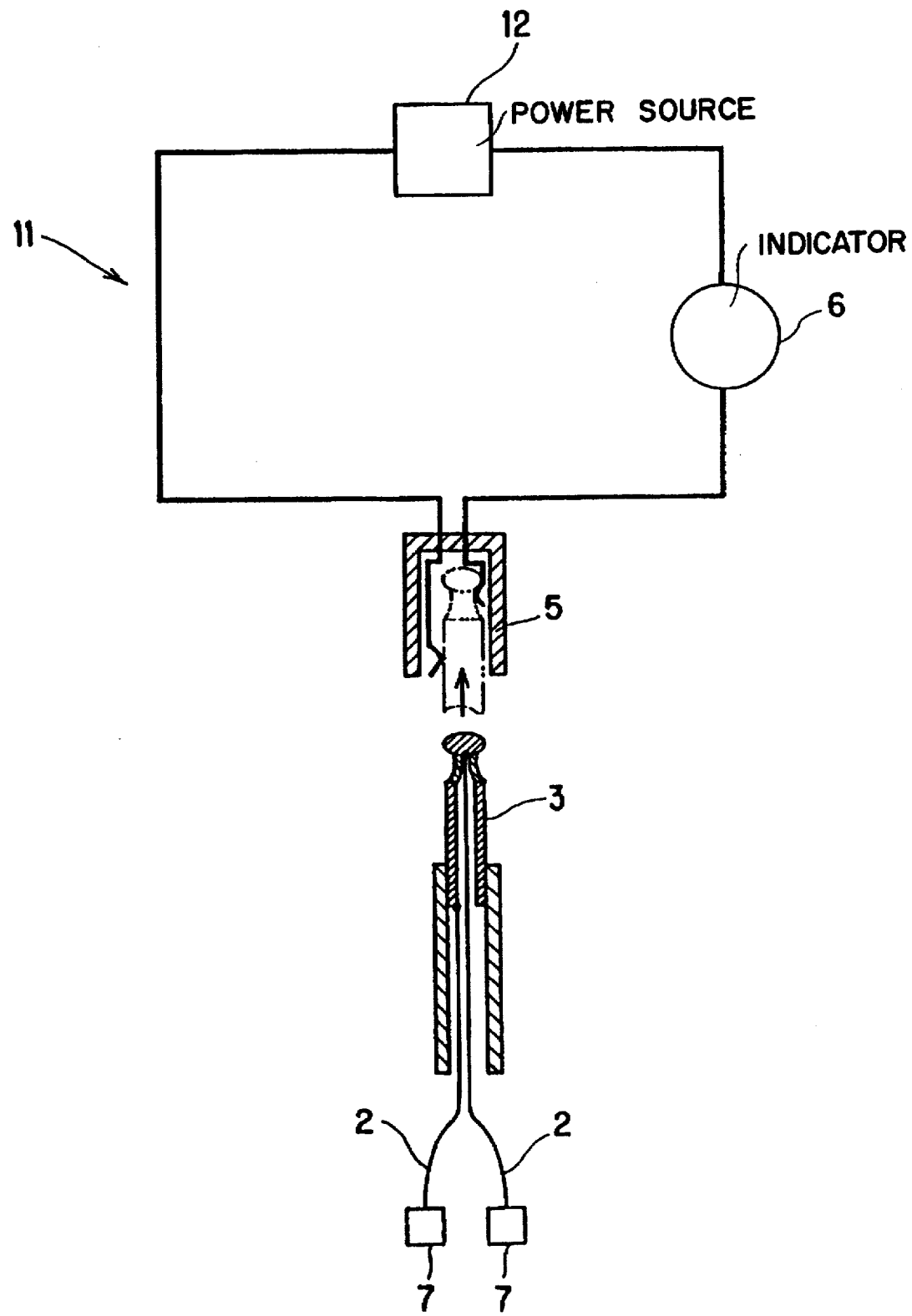
FIG. 2 is a view showing an embodiment of a basic circuit of the disconnection checker shown in FIG. 1.

FIG. 2 shows an embodiment of a basic circuit of the disconnection checker of lead cords. In the circuit 11 for checking disconnection, the terminal 5 for checking disconnection and the indicator 6 are connected in series to a power source 12, and the terminal 5 for checking disconnection alone is opened.

When each lead cord 2 is checked for disconnection, the jack 3 of the lead cord 2 to be checked is inserted into the terminal 5 for checking disconnection and the two leads 7, 7 formed at the tip of the lead cord 2 are short-circuited. If the lead cord 2 is not disconnected, the disconnection-checking circuit 11 is closed so as to trigger indicator 6, thereby it can readily be known that the checked lead cord 2 is not disconnected.

In contrast, if the lead cord 2 is disconnected, the disconnection-checking circuit 11 is not closed even when the two leads 7, 7 formed at the tip of the lead cord 2 are short-circuited, so that indicator 6 is not triggered, thereby it can be known that the checked lead cord 2 is disconnected.

It should be noted that the structures of the jack 3 and the terminal 5 for checking disconnection are not restricted to those shown in FIG. 2, and those having appropriate structures may be employed. As the power source, ordinary dry cells may be used. In case of using a commercial AC power, the power source 12 may be provided with the function of transformer or rectifier. Further, a switch for opening and closing the disconnection-checking circuit 11 may be provided so as to pass electric current through the disconnection-checking circuit only when the lead cord 2 is checked for disconnection.

Figure 3:
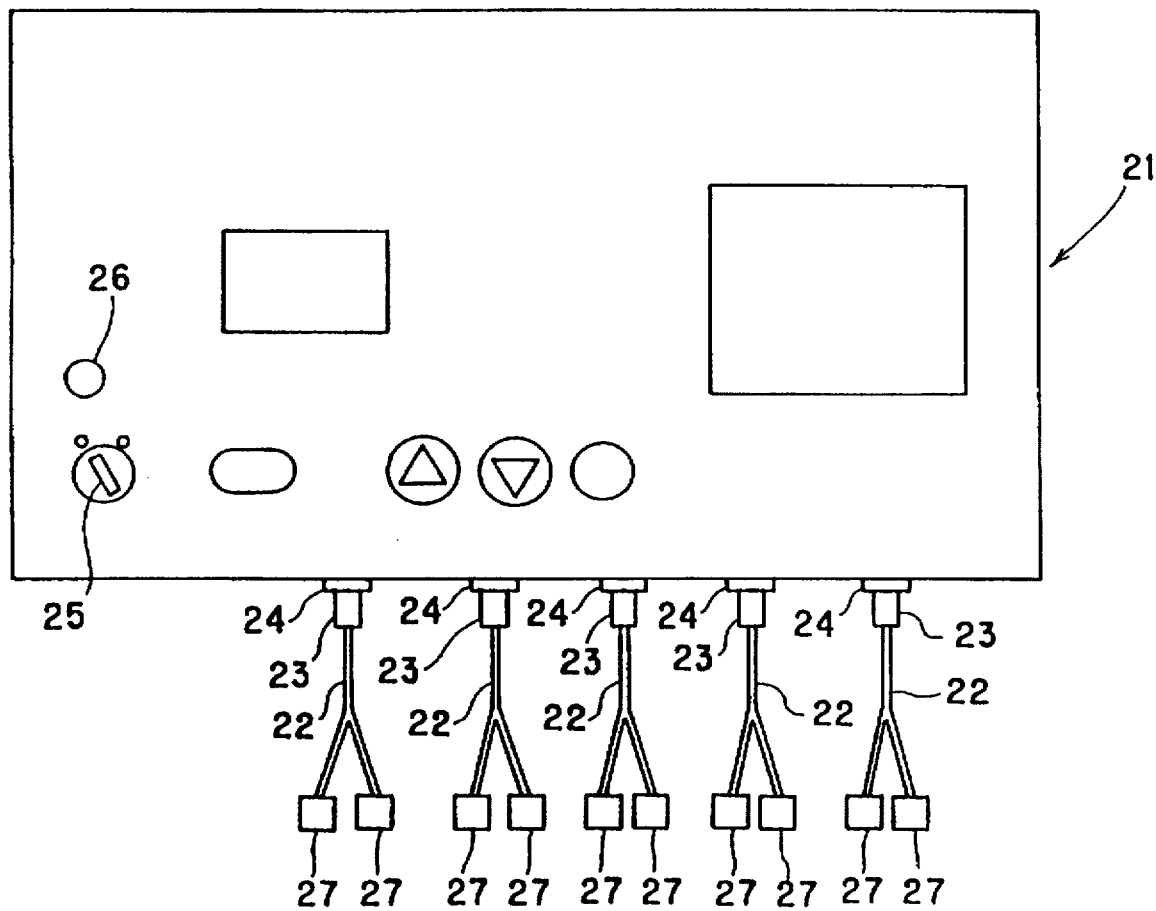
FIG. 3 is a plan view showing the entirety of another embodiment of the disconnection checker of lead cords in low-voltage output type low-frequency beautifying apparatuses, according to the present invention.

FIG. 3 is a plan view showing another embodiment of the disconnection checker of lead cords in a box type low-voltage output type low-frequency beautifying apparatus. In the front face of a main body 21 of the low-voltage output type low-frequency beautifying apparatus, a plurality of terminals 24 into which a jack 23 of each of a plurality of lead cords 22 corresponding to a prescribed sites of human body to be beautified are formed, as in the first embodiment described above.

On the upper face of the main body 21 of the low-voltage output type low-frequency beautifying apparatus, a change-over switch 25 used when checking disconnection of each of the lead cords 22, and an indicator 26 which is triggered when the lead cord 22 is not disconnected are provided.

Figure 4:
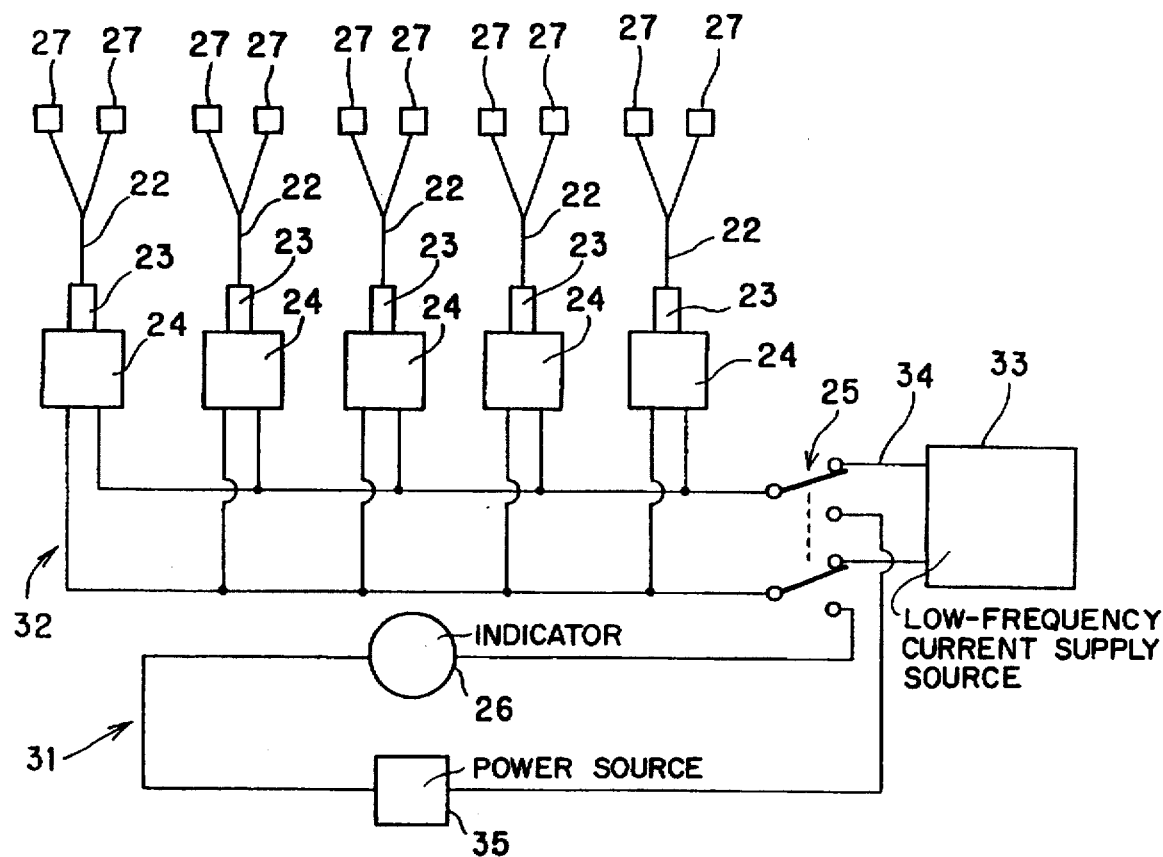
FIG. 4 is a view showing an embodiment of a basic circuit of the disconnection checker shown in FIG. 3.

FIG. 4 shows an embodiment of a circuit of the disconnection checker of lead cords in a box type low-voltage output type low-frequency beautifying apparatus. This circuit 31 for checking disconnection is connected, via the change-over switch 25, to a low-frequency current-supplying circuit 32 which supplies prescribed low-frequency electric current to each of the lead cords 22 via each lead 24 and each jack 23. That is, in the line 34 which connects the low-frequency current supply source 33 and the plurality of leads 24, a power source 35 and the above-mentioned indicator 26 are provided via the change-over switch 25. Thus, when the change-over switch 25 is switched to the side of the disconnection-checking circuit 31, the power source 35, indicator 26 and each of the lead cords 22 are connected in series.

When each lead cord 22 is checked for disconnection, the change-over switch 25 is switched to the side of the disconnection-checking circuit 31, and leads 27, 27 of an optional lead cord 22 are short-circuited without short-circuiting the leads of other lead cords 22. If the lead cord 22 is not disconnected, the disconnection-checking circuit 31 which triggers indicator 26 is closed. Therefore, by triggering indicator 26, it is known that the tested lead cord 22 is not disconnected. When the leads 27, 27 of the respective lead cords 22 are short-circuited sequentially, the indicator 26 is triggered respectively, if the respective tested lead cord 22 is not disconnected.

If the lead cord 22 is disconnected, the disconnection-checking circuit 31 which triggers indicator 26 is not closed even when the two leads 27, 27 formed at the tip of the lead cord 22 are short-circuited, so that indicator 26 is not triggered. By this, it is known that the lead cord 22 is disconnected.

In the preferred, embodiment, an LED lamp is used as the indicator 26.

However, in the present invention, other light-emitting devices, sound-making devices such as buzzers, electric current-measuring devices such as ampere meters may be employed in place of an LED lamp.

When a buzzer is employed, whether the lead cord 22 is disconnected or not can be known from whether the buzzer makes sound or not. When an ampere meter is employed, whether the lead cord 22 is disconnected or not can be known from the movement of the hand of the ampere meter. These indicator means may be used in combination. Although it is preferred to arrange the indicator 6, 26, on the upper face of the low-voltage output type low-frequency beautifying apparatus when the apparatus is relatively small because of ease of watching, the location at which the indicator is arranged is not restricted and other locations which are easy to watch, such as the front face of the apparatus, may be selected depending on the shape and size of the main body 1 of the beautifying apparatus, the location at which the beautifying apparatus is placed, and so on.

INDUSTRIAL AVAILABILITY

As described above, the disconnection checker of lead cords in low-voltage output type low-frequency beautifying apparatus according to the present invention is useful for checking disconnection of a lead cord in advance of the beautification operation. The disconnection checker according to the present invention is especially suited for low-voltage output type low-frequency beautifying apparatuses whose output is about 1 mA and 6–9V.

I claim:

1. A disconnection checker of lead cords in low-voltage output type low-frequency beautifying apparatuses which carry out beautification by attaching two leads to a human body, which leads are connected to a lead cord, and passing low-voltage and low-frequency current through the leads, said disconnection checker comprising:

a terminal for checking disconnection arranged in a main body of said low-voltage output type low-frequency beautifying apparatus;

a power source for supplying power to said terminal; and indicator means connected to said terminal for indicating disconnection, wherein whether the lead cord is disconnected or not is known from indication of said indicator means when a jack of said lead cord is inserted into said terminal for checking disconnection and said two leads connected to said lead cord are short-circuited.

2. The disconnection checker according to claim 1, wherein said indicator means is a light-emitting device.

3. The disconnection checker according to claim 1, wherein said indicator means is a sound-making device.

4. The disconnection checker according to claim 1, wherein said indicator means is a device for measuring electric current.

5. A lead cord disconnection testing device for indicating when a lead cord has a discontinuity in a low-voltage output type low-frequency beautifying apparatus which performs beautification by attaching two leads stemming from one end of the lead cord to a human body and passing low-voltage and low-frequency current through the leads, said lead cord disconnection testing device comprising:

a terminal for receiving one end of the lead cord;

a power source for supplying power to said terminal; and indicator means for indicating, during a testing mode, whether the lead cord has a discontinuity based on whether or not the power supplied to said terminal reaches said indicator means; and a change-over switch which, during the testing mode, is switched ON to provide a connection between said power source and said terminal to enable lead cord disconnection testing, said two leads stemming from said lead cord being short-circuited during the testing mode.

6. The lead cord disconnection testing device according to claim 5, wherein said indicator means is a light-emitting device.

7. The lead cord disconnection testing device according to claim 5, wherein said indicator means is a sound-making device.

8. The lead cord disconnection testing device according to claim 5, wherein said indicator means is a device for measuring electric current.

9. A lead cord discontinuity testing device for indicating when a lead cord has a discontinuity, the lead cord having a jack at one end which allows connection of the lead cord to an electrical device and two leads stemming from the other end of the lead cord, the two leads being short-circuited during a testing mode, said lead cord discontinuity testing device comprising;

an input terminal in which the lead cord jack is inserted to connect the lead cord to said terminal;

a power source for supplying power to said input terminal;

an indicator, connected to said input terminal, said indicator receiving power from said power source via said input terminal when the lead cord coupled to said input terminal does not have a discontinuity, and not receiving power from said power source via said input terminal when the lead cord coupled to said input terminal has a discontinuity.

10. The lead cord discontinuity testing device of claim 9, wherein said power source, said input terminal, and said indicator are connected in series so that, when the lead cord coupled to said input terminal does not have a discontinuity, a closed loop is formed so that current flows from said power source through said terminal, to said indicator.

11. The lead cord discontinuity testing device of claim 9, wherein the electrical device is a beautifying device, said input terminal is located on the face of said beautifying device, and said power supply is positioned inside said beautifying device.

12. The lead cord discontinuity testing device of claim 11, wherein said indicator is a light-emitting diode positioned on the face of the beautifying device.

13. The lead cord discontinuity testing device of claim 9, wherein the electric device has an operating mode and a testing mode and said input terminal is used for both the operating mode and the testing mode.

14. The lead cord discontinuity testing device of claim 13, further comprising:

a change-over switch which is switched ON during the testing mode to connect said power supply and said input terminal and is switched OFF during an operating mode to connect an operating mode power source to said input terminal.

15. The lead cord discontinuity testing device of claim 13, wherein said electrical device is a beautifying apparatus.

16. The lead cord discontinuity testing device of claim 15, further comprising:

a change-over switch which is switched ON during the testing mode to connect said power supply and said input terminal and is switched OFF during an operating mode to connect a beautification treatment power source to said input terminal.

* * * * *